(12) United States Patent
Sievert et al.

(10) Patent No.: US 8,461,378 B2
(45) Date of Patent: Jun. 11, 2013

(54) PURIFICATION OF FLUOROALKANESULFONATE SALTS

(75) Inventors: Allen Capron Sievert, Elkton, MD (US); Lee Grant Sprague, Augusta, GA (US); James A. Schultz, Swedesboro, NJ (US); Katelyn Rae Walck, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 340 days.

(21) Appl. No.: 12/879,553

(22) Filed: Sep. 10, 2010

(65) Prior Publication Data

US 2012/0065425 A1 Mar. 15, 2012

(51) Int. Cl.
*C07C 309/10* (2006.01)

(52) U.S. Cl.
USPC .......................................... 562/111; 562/113

(58) Field of Classification Search
USPC .................................................. 562/111, 113
See application file for complete search history.

(56) References Cited

U.S. PATENT DOCUMENTS

| | | | |
|---|---|---|---|
| 2,403,207 A | 7/1946 | Barrick et al. | |
| 5,013,778 A | 5/1991 | Bath | |
| 5,112,894 A | 5/1992 | Bath | |
| 5,376,516 A | 12/1994 | Mochizuki et al. | |
| 5,518,788 A | 5/1996 | Invie | |
| 5,877,796 A | 3/1999 | Tsuchiya et al. | |
| 6,171,774 B1 | 1/2001 | Hiyama et al. | |
| 6,835,780 B2 | 12/2004 | Aimura et al. | |
| 6,908,722 B2 | 6/2005 | Ebata et al. | |
| 7,288,359 B2 | 10/2007 | Iwasawa et al. | |
| 7,291,663 B2 | 11/2007 | Hattori et al. | |
| 7,297,813 B2 | 11/2007 | Smith et al. | |
| 7,897,807 B2 * | 3/2011 | Harmer et al. | 562/113 |
| 2002/0155964 A1 | 10/2002 | Amemiya et al. | |
| 2003/0113658 A1 | 6/2003 | Ebata et al. | |
| 2003/0236330 A1 | 12/2003 | Hattori et al. | |
| 2006/0030725 A1 | 2/2006 | Smith et al. | |
| 2006/0272950 A1 | 12/2006 | Martyak et al. | |
| 2006/0276671 A1 | 12/2006 | Harmer et al. | |
| 2009/0035655 A1 | 2/2009 | Gambut-Garel et al. | |
| 2010/0033899 A1 | 2/2010 | Koh et al. | |

FOREIGN PATENT DOCUMENTS

| | | |
|---|---|---|
| EP | 0679945 A2 | 4/1995 |
| EP | 0336573 B1 | 7/1995 |
| EP | 0752711 A1 | 1/1997 |
| EP | 0679945 B1 | 8/1998 |
| EP | 0556002 B1 | 12/1998 |
| EP | 0742109 B1 | 3/1999 |
| EP | 0752711 B1 | 10/1999 |
| EP | 1270553 B1 | 11/2009 |
| JP | 11242316 A | 9/1999 |
| JP | 11244705 A | 9/1999 |
| JP | 2004053898 A | 2/2001 |
| JP | 2002167500 A | 6/2002 |
| JP | 2003192661 A | 7/2003 |
| WO | 2004/101860 A1 | 11/2004 |
| WO | 2005/033150 A1 | 4/2005 |

OTHER PUBLICATIONS

D. D. Coffman, et al. "Addition Reactions of Tetrafluoroethylene," Contribution No. 258 from The Chemical Department, Experimental Station, E.I. Du Pont De Nemours and Company, Inc. pp. 747-753, (1949).

* cited by examiner

*Primary Examiner* — Johann R Richter
*Assistant Examiner* — Kofi Adzamli
(74) *Attorney, Agent, or Firm* — Kevin J. Boland

(57) ABSTRACT

A process for the purification of fluoroalkanesulfonate salt comprising (a) contacting a mixture of said salt and an inorganic salt contaminant with a solvent to selectively dissolve said fluoroalkanesulfonate salt in solution, and (b) isolating the solution, to yield a fluoroalkanesulfonate salt containing less than 500 micrograms of inorganic salt contaminant per gram of fluoroalkanesulfonate salt, or containing less than a maximum of 0.3% by weight of individual solvent.

18 Claims, No Drawings

PURIFICATION OF FLUOROALKANESULFONATE SALTS

FIELD OF THE INVENTION

This invention relates to a process for the purification of fluoroalkanesulfonate salts. More specifically, this invention provides a process for the removal of solvent and inorganic salt contaminants from fluoroalkanesulfonate salts.

BACKGROUND OF THE INVENTION

Fluoroalkanesulfonate salts find diverse applications in areas such as photoacid generators, battery electrolytes, antistatic agents, flame retardants, and as precursors for fluorinated sulfonic acids and ionic liquids. For many of these applications, it is essential that the fluoroalkanesulfonate salts be highly pure and free of both organic and inorganic contaminants.

U.S. Patent Application 2006/0276671 discloses a process for the preparation of hydrofluoroalkanesulfonic acid by reaction of a fluoroolefin with an aqueous sulfite solution having a pH 4 to 12, and isolating the acid by distillation. In this disclosure acetone was employed as an extraction solvent. Fluoroalkanesulfonate salts prepared by these procedures may contain significant amounts of solvent or salt contaminants which are carried over from the synthetic process. There is a need for practical processes that provide highly pure fluoroalkanesulfonate salts.

BRIEF SUMMARY OF THE INVENTION

The present invention comprises a process for the purification of fluoroalkanesulfonate salts comprising
(a) contacting a mixture comprising
1) at least one fluoroalkanesulfonate salt of the formula

$$[C(H)(F)(X)CF_2SO_3]_yM \qquad (I)$$

wherein
X is H, Cl, F, $CF_3$, or OR;
R is $C_1$-$C_6$ alkyl, fluoroalkyl, or perfluoroalkyl;
M is Li, Na, K, Cs, Rb, Ca, or Ba; and
y is a positive integer equal to the valence of M; and
2) at least one inorganic salt contaminant,
with one or more solvents to selectively dissolve at least a portion of said salt in solution;
(b) isolating the solution from the mixture to yield a fluoroalkanesulfonate salt containing less than 500 micrograms of inorganic salt contaminant per gram of fluoroalkanesulfonate salt, or containing less than a maximum of 0.3% by weight of individual solvent.

The present invention further comprises the above process having an additional step which is (c) mixing said solution of fluoroalkanesulfonate salt with a diluent followed by removal of said solvent, and isolation of the fluoroalkanesulfonate salt. The diluent can be recycled back into the process.

The present invention further comprises the above process wherein prior to step (a) a mixture comprising at least one fluoroalkanesulfonate salt as defined above and at least one contaminant is contacted with water and an oxidizing agent to convert any sulfite and bisulfite salts present to sulfate salts, followed by removal of the water. The resulting mixture is then contacted with solvent as described above in step (a).

The present invention further comprises any of the above-described processes wherein the solvent is recovered after use and recycled in the process.

DETAILED DESCRIPTION OF THE INVENTION

The present invention provides a process for the removal of inorganic salt contaminants from fluoroalkanesulfonate salts. In addition the present invention provides a process for the removal of solvent contaminants from fluoroalkanesulfonate salts. Fluoroalkanesulfonate salts purified by this invention include those of the formula (I)

$$[C(H)(F)(X)CF_2SO_3]_yM \qquad (I)$$

wherein M is Li, Na, K, Cs, Rb, Ca, or Ba; X is H, Cl, F, $CF_3$, or OR; and R is $C_1$-$C_6$ alkyl, $C_1$-$C_6$ fluoroalkyl, or $C_1$-$C_6$ perfluoroalkyl; and y is a positive integer equal to the valence of M. Examples of fluoroalkanesulfonate salts used in the process of this invention include $CHClFCF_2SO_3Li$, $CHClFCF_2SO_3Na$, $CHClFCF_2SO_3K$, $CHF_2CF_2SO_3Li$, $CHF_2CF_2SO_3Na$, $CHF_2CF_2SO_3K$, $(CHF_2CF_2SO_3)_2Ca$, $(CHF_2CF_2SO_3)_2Ba$, $CF_3CHFCF_2SO_3Li_1$, $CF_3CHFCF_2SO_3Na$, $CF_3CHFCF_2SO_3K$, $(CF_3CHFCF_2SO_3)_2Ba$, $CF_3OCHFCF_2SO_3Li$, $CF_3OCHFCF_2SO_3Na$, $CF_3OCHFCF_2SO_3K$, $C_2F_5OCHFCF_2SO_3Li_1$, $C_2F_5OCHFCF_2SO_3Na$, $C_2F_5OCHFCF_2SO_3K$, $C_3F_7OCHFCF_2SO_3Li_1$, $C_3F_7OCHFCF_2SO_3Na$, and $C_3F_7OCHFCF_2SO_3K$.

These fluoroalkanesulfonate salts are prepared by the reaction of fluorinated olefins of the formula $CFX=CF_2$, where X is as defined above, with an aqueous solution of sulfite and bisulfite salts as disclosed by Barrick in U.S. Pat. No. 2,403,207 and Junk, et. al. in U.S. Patent Application 2006/0276671. For example, a fluoroolefin is reacted with an aqueous sulfite solution having a pH of 4 to 12 to generate the hydrofluoroalkane sulfonate salt, which is then converted to the corresponding sulfonic acid. The teachings of these disclosures are hereby incorporated by reference. Said reaction of fluorinated olefins with an aqueous solution of sulfite and bisulfite salts provides an aqueous product mixture comprising the fluoroalkanesulfonate salts and the unreacted sulfite and bisulfite salts in addition to any olefin hydrolysis products and reaction by-products. Reaction by-products may include carboxylate salts of the formula $CHFXCO_2M$ and fluoride and/or bifluoride salts, MF and $MHF_2$ where X and M are as defined above in formula (I), and sulfite and bisulfite oxidation products which include sulfate salts. Inorganic salt contaminants, herein referred to as "M-salt contaminants", which can be present include one or more M-salts selected from the group consisting of chlorides, fluorides, hydroxides, carbonates, hydrogen carbonates, sulfates, sulfites, hydrogen sulfites, borates, phosphates, monohydrogen phosphate, and dihydrogen phosphate where M is as defined above. The inorganic salt contaminants can be present as impurities or intentionally added to the reaction mixture as buffering agents in accordance with teachings in the art.

As disclosed in U.S. Patent Application 2006/0276671, the reaction conditions for synthesis of fluoroalkanesulfonate salts can be chosen in such a way as to permit precipitation of the fluoroalkanesulfonate salt from the reaction solution when it is cooled. In this case the precipitated fluoroalkanesulfonate salt is isolated by filtration using techniques well known in the art. The isolated salt is then dried. Such a precipitated salt is considered to be crude since it typically contains M-salt contaminants. It is not necessary that the isolated crude fluoroalkanesulfonate salt be completely dry, though preferably the crude product contains less than about 5 weight percent water, and preferably less than 1 weight percent water.

The present invention provides a process for the removal of solvent and/or inorganic salt contaminants from a fluoroalkanesulfonate salt. The process comprises (i) contacting a solid mixture comprising (a) one or more fluoroalkanesulfonate salts of the formula $[C(H)(F)(X)CF_2SO_3]_yM$ wherein M is Li, Na, K, Cs, Rb, Ca, or Ba; X is H, Cl, F, $CF_3$, or OR; R is $C_1$-$C_6$ alkyl, fluoroalkyl, or perfluoroalkyl; and y is a positive integer equal to the valence of M; and (b) one or more M-salt contaminants selected from the group consisting of chlorides, fluorides, hydroxides, carbonates, hydrogen carbonates, sulfates, sulfites, hydrogen sulfites, borates, phosphates, monohydrogen phosphate, and dihydrogen phosphate where M is as defined above, with a solvent or a solvent mixture. This results in selectively separating component (a) from component (b) in said mixture by dissolving at least a portion of the fluoroalkanesulfonate salt in said solvents to provide a solution of the fluoroalkanesulfonate salt, and leaving the M-salt contaminants in the undissolved solid. This step (a) is then followed by (b) isolating said solution of the fluoroalkanesulfonate salt from the solid containing the M-salt contaminants. The isolating or separating can be carried out by any conventional means, such as by filtering and then evaporating said solution of the fluoroalkanesulfonate salt in the presence of water followed by drying to provide a dry, purified fluoroalkanesulfonate salt. Alternatively the isolation can be carried out by treating said separated solution of the fluoroalkanesulfonate salt with sufficient water to dissolve the fluoroalkanesulfonate salt, followed by distilling said solvent from the mixture to provide an aqueous solution of the fluoroalkanesulfonate salt, which is then evaporated and dried to provide a dry, purified fluoroalkanesulfonate salt. This invention also provides a fluoroalkanesulfonate salt with reduced concentrations of solvent and/or inorganic salt contaminants.

The present invention provides a process for the removal of M-salt contaminants from a solid mixture of fluoroalkanesulfonate salts. In step (a) of the process, the solid mixture comprising fluoroalkanesulfonate salts and one or more M-salt contaminants is contacted with a solvent or solvent mixture to form a slurry. The slurry comprises the fluoroalkanesulfonate salts dissolved in the solvent or solvent mixture and the solid one or more M-salt contaminants as well as any undissolved fluoroalkanesulfonate salts. Solvents suitable for the process of the invention include acetone, methyl ethyl ketone, methanol, ethanol, isopropanol, acetonitrile, ethyl acetate, tetrahydrofuran, 1,2-dimethoxyethane, and dimethyl carbonate, or mixtures thereof. Preferred solvents include acetone, methanol, and ethanol. If the solubility of the fluoroalkanesulfonate salts in the preferred solvent is low (e.g., less than about 20 weight percent), a small amount of water (e.g., less than about 2 weight percent) may be added to the solvent or solvent mixture to enhance the solubility of the fluoroalkanesulfonate salt. It is preferable that the water be totally miscible with the solvent or solvent mixture.

The contacting step (a), also designated herein as an extraction, is carried out at a temperature of from about 20° C. to the boiling point of the solvent mixture. Often for simplicity and ease in further processing steps, the solvent extraction is carried out at ambient temperature (e.g., from about 20° C. to about 30° C.). However, since the solubility of fluoroalkanesulfonate salts increases with temperature, carrying out the extraction at elevated temperature can increase the efficiency of this step (a) of the process.

Normally the contacting is conducted in a batch manner in a vessel provided with an agitator to enable good mixing between the solvent and the solid mixture. However, continuous extraction devices, such as Soxhlet extraction, can be employed as well. The reactor, its feed lines, effluent lines, and associated units are constructed of materials resistant to low levels of aqueous fluorides although the pH ranges encountered in this process are not extreme (from about pH 4 to about pH 10). A typical material of construction is stainless steel although polymer-lined carbon steel may be employed successfully. Glass equipment can be used as well.

In step (b) of the process, the slurry comprising the solution of the fluoroalkanesulfonate salts dissolved in the solvent or solvent mixture and the ay least one solid M-salt contaminant are separated. Said separation can be carried out using techniques well-known in the art such as by filtration or centrifugation. Any filtering medium (e.g., bags, frits, screens) may be used provided that it is stable to the solvent or solvent mixture employed. The isolated solution of fluoroalkanesulfonate salts contains less than 500 micrograms of inorganic salt contaminant per gram of fluoroalkanesulfonate salt. Preferably the salt contains less than 300 micrograms of inorganic salt contaminant per gram of fluoroalkanesulfonate salt, and more preferably less than 100 micrograms of inorganic salt contaminant per gram of fluoroalkanesulfonate salt.

Preferably sufficient solvent is employed in the extraction step to completely dissolve all of the fluoroalkanesulfonate salts in the mixture; however, multiple extraction and isolation sequences can be employed as well.

The process of the present invention can optionally further comprise drying of the fluoroalkanesulfonate salts. The solvent in said separated solution of the fluoroalkanesulfonate salt is removed in the presence of water followed by drying to provide the purified solid fluoroalkanesulfonate salt. The amount of water added to the separated solution of the fluoroalkanesulfonate salt is typically from about 1 weight percent to about 100 weight percent based on the weight of solvent employed in step (a) of the process. Water need not be added if it was initially present in the extraction step (a).

Said removal of solvent may be accomplished by any of several means using techniques known in the art such as by evaporation or distillation. This includes evaporation by purging with an inert gas, optionally with heating, or by evaporation in a rotating evaporator. Solvent removal is conducted at atmospheric or sub-atmospheric pressure. In this embodiment of the invention the solvent is preferably removed by evaporation.

Evaporation can be carried out in a stirred vessel, rotated vessel, or in an oven at atmospheric or sub-atmospheric pressure. The evaporation can be accompanied by a purge stream of air or nitrogen. For convenience the evaporation step is preferably carried out in an oven provided with trays which are filled with the solution of the fluoroalkanesulfonate salt. The evaporation is carried out at atmospheric or sub-atmospheric pressure. If flammable solvents are involved, it is preferred that the evaporation take place with a purge of inert gas such as nitrogen.

Temperatures suitable for the evaporation can be from about 20° C. to about 150° C. depending on the pressure employed. If the pressure is subatmospheric, then evaporation temperatures of from about 20° C. to about 60° C. are employed depending on the exact pressure. If the pressure is atmospheric, then evaporation temperatures of from about 50° C. to about 150° C. are suitable, preferably from about 60° C. to about 120° C. Said evaporation can be staged with the bulk of the solvent removed at lower temperature followed by a finishing step at higher temperature optionally with a grinding or milling step conducted between temperature stages. The fluoroalkanesulfonate salt after isolation contains a maximum of about 0.3% by weight of individual solvent, preferably a maximum of about 0.2% by weight of individual solvent, and more preferably a maximum of about 0.1% by weight of individual solvent.

In one embodiment of the invention, after isolating the solution of fluoroalkanesulfonate salt from the mixture in step (b), sufficient water is added to the separated solution of the fluoroalkanesulfonate salt to dissolve essentially all the fluoroalkanesulfonate salt. Amounts of water in excess of this may be employed, but are not beneficial and only serve to extend the time and amount of energy required in the drying step. After adding water to the separated solution of the fluoroalkanesulfonate salt, the solvent component of the mixture is removed. If the solvent is not water-soluble, a second liquid phase forms on addition of water and at least a portion of said removal may be effected by decantation of the water-insoluble phase. Typically, however, many of the preferred solvents or solvent mixtures are water-soluble and addition of water will not initially result in the formation of a second liquid phase.

The solvent is then removed from the mixture of fluoroalkanesulfonate salt, water, and solvent. Said removal of solvent is accomplished by any of several means using techniques known in the art. This includes evaporation by purging with an inert gas, optionally with heating, by evaporation in a rotating evaporator, by vacuum stripping, or by distillation optionally at sub-atmospheric pressure. In this embodiment, the solvent is preferably removed by distillation.

Said distillation can proceed from a stirred vessel provided with a source of heat and a condenser to enable recovery of the distilled solvent. It is not essential that all of the solvent be removed from the mixture of fluoroalkanesulfonate salt, water, and solvent. Rather it is sufficient to remove at least 90% of the solvent, preferably 95% of the solvent, and most preferably at least 99% of the solvent. Removal of solvent from the mixture of fluoroalkanesulfonate salt, water, and solvent provides an aqueous solution of the fluoroalkanesulfonate salt.

The aqueous solution of the fluoroalkanesulfonate salt, along with any remaining solvent in the mixture, is evaporated and dried to provide a fluoroalkanesulfonate salt. Said evaporation is conducted by procedures known in the art such as freeze-drying, spray-drying, distillation, or vacuum-stripping. Evaporation can be carried out in a stirred vessel, rotated vessel, or in an oven at atmospheric or sub-atmospheric pressure. The evaporation can be accompanied by a purge stream of air or nitrogen. For example, the evaporation step can be carried out in an oven provided with trays which are filled with the aqueous solution of the fluoroalkanesulfonate salt. The evaporation can be carried out at atmospheric or sub-atmospheric pressure. Temperatures suitable for the evaporation step can be from about 50° C. to about 180° C. depending on the pressure used. If the pressure is sub-atmospheric, then evaporation temperatures of from about 50° C. to about 90° C. is employed depending on the exact pressure. If the pressure is atmospheric, then evaporation temperatures of from about 100° C. to about 180° C. are suitable, preferably from about 110° C. to about 150° C. Said evaporation can be staged with the bulk of the solvent removed at lower temperature followed by a finishing step at higher temperature optionally with a grinding or milling step conducted between temperature stages.

In another embodiment, the present invention further comprises after the isolating step (b), mixing the solution of fluoroalkanesulfonate salt with a diluent followed by removal of solvent. In this embodiment the removal of solvents from the separated solution of the fluoroalkanesulfonate salt is carried out in the presence of a diluent, and optionally in the presence of water. Preferably the diluent is soluble in the solvent of step (a) and has a higher boiling point than the solvent or solvent mixture. Also, it is preferred that the fluoroalkanesulfonate salt is substantially insoluble in the diluent. Examples of diluents suitable for this embodiment of the invention include alkanes, arenes, halogenated hydrocarbons, halogen-substituted arenes, aliphatic ethers, aliphatic esters, aliphatic carbonate esters and aliphatic ketones, each with a boiling point greater than about 90° C. and less than about 150° C. Specific diluents suitable for this embodiment of the invention include heptane, octane, toluene, xylene (including o-xylene, m-xylene, p-xylene isomers and mixtures thereof), ethylbenzene, chlorobenzene, tetrachloroethylene, di-n-butylether, butyl acetate, ethyl butyrate, diethyl carbonate, and 3-pentanone. Preferred diluents include alkyl-substituted arenes such as toluene, o-xylene, m-xylene, p-xylene, and ethylbenzene. The most preferred diluents include toluene, o-xylene, m-xylene, and p-xylene.

If water is added to the mixture of fluoroalkanesulfonate salt, solvent, and diluent, it is added in the amount of from about 1% by weight to about 25% by weight, preferably from about 5% by weight to about 20% by weight, based on the amount of diluent present. The water can be added initially or can be added after the solvent has been substantially removed from the mixture.

After the solution of the fluoroalkanesulfonate salt dissolved in the solvent has been treated with the diluent, and optionally water, the mixture is distilled to remove the solvent. As the solvent is removed from the mixture, the fluoroalkanesulfonate salt begins to precipitate. After the solvent has been substantially removed, the fluoroalkanesulfonate salt can be recovered from the mixture by filtration. Any filtering medium (e.g., bags, frits, screens) is used provided that it is stable to the solvent or solvent mixture employed.

After the solid fluoroalkanesulfonate salt has been recovered from the filtration step, any remaining traces of diluent or water in the recovered salt can be removed by a drying step. The drying step is carried out in an oven or kiln optionally under subatmospheric pressure and optionally with a purge of air or nitrogen as discussed above.

It has been found that removal of traces of solvent from the fluoroalkanesulfonate salts is facilitated by reducing the particle size of the fluoroalkanesulfonate salt prior to a final drying step. Therefore, in another embodiment the present invention further comprises reducing the particle size of the isolated solid fluoroalkanesulfonate salt prior to or during the final drying step. Said reduction of the particle size of the solid may be effected by any one of several means known in the art such as by grinding, pulverizing, or crushing. Such procedures may be accomplished using equipment known in the art such as by mortar and pestle, tumbling mills, hammer mills, or jaw crushers. A wide range of particle sizes are suitable for attaining low levels of residual solvent after drying. Free-flowing fluoroalkanesulfonate salts having a particle size diameter of a maximum of about 1 mm are typically suitable. Preferably the particle size diameter is a maximum of about 0.5 mm. Of note is the pulverizing or grinding of potassium 1,1,2,2-tetrafluoroethanesulfate acetone solvate prior to final drying step.

In yet another embodiment, the present invention further comprises prior to contacting the mixture with solvent in step (a), contacting said same mixture first with water and an oxidizing agent to convert any sulfite and bisulfite salts present to sulfate, followed by removal of the water. Unreacted sulfite and bisulfite salts (i.e., oxysulfur species in the +4 oxidation state) in the aqueous mixture of fluoroalkanesulfonate salt and contaminant are oxidized to a mixture of sulfate salts (i.e., oxysulfur species in the +6 oxidation state). Said oxidation is carried out by treating said aqueous mixture of fluoroalkanesulfonate salt and contaminant with an oxidizing agent such as air (oxygen), aqueous hydrogen peroxide, aqueous persulfate salts, aqueous sodium hypochlorite, chlorine, or chlorine dioxide. Preferably the oxidizing agent is an aqueous solution of hydrogen peroxide having a concentration of from about 1% by weight to about 50% by weight, preferably from about 3% by weight to about 30% by weight. The oxidation is carried out at a temperature of from about 10° C. to about 100° C., preferably from about 15° C. to about 40° C., by adding the aqueous solution of hydrogen peroxide solution to the aqueous mixture with stirring. The hydrogen peroxide is added in a amount sufficient to convert all of the sulfur species in the +4 oxidation state to sulfur species in the +6 oxidation state. Although a slight excess of hydrogen peroxide can be used, a large excess of hydrogen peroxide is not advantageous. Preferably unreacted hydrogen peroxide remaining after treating the mixture is destroyed by stirring at about 20° C. to about 30° C. for an extended period or by heating the mixture to about 50° C. to about 100° C.

If the oxidizing agent is oxygen (in the form of air), the oxygen is purged into the aqueous mixture for a time sufficient to convert the sulfur species in the +4 oxidation state to sulfur species in the +6 oxidation state. Oxidation of the sulfur species in the +4 oxidation state to sulfur species in the +6 oxidation state can result in precipitation of the sulfate salts which can optionally be separated from the solution by filtration prior to further processing.

Typically water is removed from said aqueous product mixture comprising the fluoroalkanesulfonate salts and the unreacted sulfite and bisulfite salts, optionally in the oxidized forms of sulfate, in addition to any other M-salt contaminants and by-products as noted above. Water removal is conducted by techniques and procedures known in the art such as freeze-drying, spray-drying, azeotropic drying, evaporation, or vacuum-stripping. Evaporation procedures can be carried out in a stirred vessel, rotated vessel, or in an oven at atmospheric or sub-atmospheric pressure. The evaporation can be accompanied by a purge stream of air or nitrogen. Whether isolated by evaporation or by filtration, the reaction of fluorinated olefins with aqueous sulfite and bisulfite salts gives a crude, solid mixture comprising fluoroalkanesulfonate salts, which is then purified by steps (a) and (b) of the process of the present invention as previously described.

In another embodiment, the process of the present invention further comprises recovery of the used solvent and recycle of said solvent. Said evaporated solvent is collected and recycled to step (a) for subsequent extractions. The solvent is collected by conventional means after its removal from the isolated solution of fluoroalkanesulfonsate salt. Removal of the solvent from the salt is as discussed above. The solvent can then be immediately reused in step (a) of the process, or stored and later used in step (a) of the process.

In another embodiment, the process of the invention further comprises recovery of the used diluent and recycle of the diluent back into the process. Said diluent is recovered after filtration of the precipitated fluoroalkane sulfonate salt, and is collected. It can be immediately recycled for subsequent extractions, or can be stored and used later.

This invention is useful to provide a fluoroalkanesulfonate salt with reduced concentrations of inorganic salt contaminants. More specifically, this invention provides fluoroalkanesulfonate salt in which the concentration of the individual M-salt contaminants is less than 500 micrograms per gram, preferably less than 300 micrograms per gram, more preferably less than 200 micrograms per gram, and most preferably less than 100 micrograms per gram.

This invention further provides a fluoroalkanesulfonate salt with reduced concentrations of solvent contaminants. More specifically, this invention provides fluoroalkanesulfonate salt in which the concentration of the solvent contaminants are individually less than 0.3% by weight, preferably less than 0.2% by weight, and most preferably less than 0.1% by weight.

EXAMPLES

In the examples the following abbreviations are used:
KDFA: Potassium 2,2-difluoroacetate $CHF_2CO_2K$
HFP: Hexafluoropropene, $CF_3CF=CF_2$
HFPSK: Potassium 1,1,2,3,3,3-hexafluoropropane-sulfonate, $CF_3CHFCF_2SO_3K$
TFE: Tetrafluoroethene, $CF_2=CF_2$
TFESK: Potassium 1,1,2,2-tetrafluoroethanesulfonate $CHF_2CF_2SO_3K$ The following materials were used in the Examples herein.

Synthesis of TFESK

A sulfite solution was prepared which consisted of 1.95 kg of potassium sulfite monohydrate ($K_2SO_3.H_2O$), 7.53 kg of potassium metabisulfite ($K_2S_2O_5$), and 21.58 liters of demineralized water. This was charged to a 10 gallon (37.85× $10^{-3}$ cubic meter) stainless steel stirred reactor equipped with a pH probe. The vapor space was evacuated and filled with nitrogen to 15 psig (201746.3 Pa) three times and finally re-evacuated. The reaction mixture was heated to 120° C. and TFE was added to the reactor; the pressure was maintained at 40 psig (377115.3 Pa). TFE (8.91 kg) was fed for 11 hours until the pH became greater than 9. The reactor was allowed to cool to 80° C. over two hours. While cooling, some residual TFE reacted; the final pH was 12. The vapor space was evacuated and filled with nitrogen and the liquid contents discharged to give 33.3 kg of clear colorless liquid. Analysis of the reaction solution by $^{19}F$ NMR indicated that it contained 44.65 weight percent TFESK and 0.061 weight percent KDFA. The sulfite concentration was determined to be 2.81 weight percent and fluoride content was 311 micrograms per gram.

The sulfite was converted to sulfate by reaction with hydrogen peroxide by adding the calculated amount of 30% aqueous hydrogen peroxide (884 g) to the reaction solution with mechanical stirring at such a rate that the temperature remained less than 75° C. White solid began to precipitate and the entire mass was transferred to a stainless steel tray and dried in an oven at 104° C. under a stream of nitrogen. When the bulk water had been removed, the solid cake was ground to a powder. The powder was further dried in the oven at 70 mm Hg ($93.3 \times 10^2$ Pa) vacuum until the amount of water found by Karl Fisher analysis was less than 25 micrograms per gram.

Synthesis of HFPSK

A solution of potassium hydroxide pellets (333.5 g, 87%, 5.171 moles) dissolved in water (2619 g) was poured into a one gallon Hastelloy™ C autoclave equipped with an impellor. The autoclave was sealed, pressure-checked with nitrogen, and purged three times with nitrogen. After venting the autoclave to 0 psig (0 Pa), the autoclave was evacuated and $SO_2$ (298 g, 4.65 moles) was added over the course of 1 h at 20-25° C. with water cooling. The pressure in the autoclave at the end of the $SO_2$ addition was about 2.7 psia (18615.8 Pa). Nitrogen was added to bring the pressure to 0 psig and a sample was taken; the pH of the solution was 5.99.

Hexafluoropropylene (HFP) was then added with stirring to a pressure of 51 psig (20 g) at 21.2° C. The autoclave was warmed to 80.0° C. (51 psig, 351632.6 Pa) over the course of 41 minutes. The reactor pressure was then increased to 65 psig (448159.2 Pa) with HFP and a total of 410 g (2.73 moles) of HFP was added over the course of 6.78 hours.

The following day, the autoclave was warmed to 57° C. and the product discharged as a homogeneous solution. The pH of the product was 6.39 (46° C.). $^{19}$F NMR analysis indicated that it contained 0.825 mmole HFPSK/g (22.3 weight percent) and 0.0168 mmole fluoride/g (0.098 weight percent). The product liquid was poured into three 190 mm×100 mm crystallizing dishes and dried at 99-105° C. for four days. The resulting dried, crude product weighed 982 g.

Example 1

This example demonstrates the removal of acetone from TFESK acetone solvate by evaporation from an aqueous solution. A 5 liter three-neck round bottom flask was equipped with a mechanical stirrer, a TC well, and a condenser connected to a nitrogen bubbler. The flask was charged with crude TFESK (482.2 g, containing about 10 weight percent potassium sulfate) and acetone (2,180 g). The flask was sealed, stirred at 300 rpm, and heated to 40-43° C. for 3.5 hours. The mixture was then filtered to give a cloudy filtrate. The solid retained on the frit was washed with 200 g of acetone. The solid was collected in a beaker, allowed to dry in the hood, and then dried in the oven to give 57.0 g of acetone-insoluble solid. The combined filtrates were re-filtered through Celite™ filter aid. The resulting clear filtrate was then rotary-evaporated to give a white, finely crystalline solid (450 g) which was dried over night in an nitrogen-purged oven at 102° C. to give 416.3 g of TFESK acetone solvate. A sample of TFESK acetone solvate (31.2 g, containing 4.4 wt % acetone) was placed in a beaker with a stirring bar. Water (30 mL) was added and the mixture stirred until the TFESK was almost dissolved; an additional 10 mL of water was and the solution was filtered. The clear filtrate was poured into a stainless steel tray. The tray was placed in a nitrogen-purged oven heated to 100° C. for 18.5 hours (atmospheric pressure). The tray was removed and the residue broken up with a spatula. The tray was returned to the oven and heated at 106° C. for an additional 6 hours. $^1$H NMR analysis of the recovered TFESK (28.6 g) indicated that only a trace of acetone was present in the sample.

Example 2

This example demonstrates purification of crude TFESK by acetone extraction followed by evaporation from an aqueous solution. A 2 L three neck round bottom flask was equipped with a mechanical stirrer, a thermocouple well, and a condenser. The top of the condenser was connected to a nitrogen-purged bubbler. The flask was charged with crude TFESK (166.17 g, containing about 10 weight percent potassium sulfate) prepared as described above. After purging with nitrogen, acetone (876.7 g, 1108 mL) was added and the flask sealed with a glass stopper. The white mixture was stirred at 300 rpm for two hours at 20.5° C.

The mixture was then filtered and the retained solid was washed with three portions of acetone. The filtrate was then poured into a 2 L three neck round bottom flask equipped with a large stirring bar, a thermocouple well, and a short path distillation head equipped with a one liter receiver. Acetone was distilled from the flask at 314-316 mm Hg (41.86-42.13 kPa) with the pot and head temperatures of about 35° C. After 736.4 g of distillate were collected, the receiver was replaced and 197 g of water was added to the flask. Distillation was resumed at 310-322 mm Hg (41.33-42.93 kPa) as the pot and head temperatures rose to 43° C. and 39.7° C., respectively; an additional 358.8 g of distillate was collected as the pot and head temperatures rose to 76.3° C. and 56.0° C., respectively. The pot content was cloudy, but no solid was present.

The pot content (323.1 g) was then poured into two stainless steel trays. The trays were placed into a nitrogen-purged oven at 121° C. After 20.8 h, the white, solid mass in each tray was broken up with a spatula. The trays were returned to the oven at 120° C. for an additional 25.8 h. The white product (143.5 g) was analyzed by $^1$H NMR and found to contain 0.021 wt % acetone (210 micrograms/g). Analysis of the product by ion chromatography indicated that none of fluoride, chloride, bromide, nitrite, nitrate, sulfate, phosphate, acetate, formate, and oxalate ions were present above 1 microgram per gram.

Example 3

This example demonstrates purification of crude TFESK by acetone extraction followed by evaporation from aqueous solution. A 22 liter round bottom flask equipped with a large magnetic spinbar was charged with 13.2 L of acetone. Over a two hour period was added 2.00 kg of crude TFESK (prepared as described above) with vigorous stirring. The mixture was stirred for an additional three hours and settled overnight. The hazy supernatant was filtered through a medium fritted filter containing a pad of Celite™ to yield a clear, colorless solution.

A 12 L round bottom flask equipped with a magnetic spinbar, equalizing pressure addition funnel, and Claisen head still was charged with 2.0 kg of demineralized water. The filtrate was added to the flask and the acetone simultaneously distilled off until the pot temperature reached 93° C. The distillation residue was hazy with suspended solids. It was combined with the residues from 3½ similar batches and suction filtered through a medium porous fritted filter covered with Celite™ filter aid to yield 11.9 kg of clear and colorless solution. $^1$H and $^{19}$F NMR assay found 2.7 weight percent acetone and 49 weight percent TFESK. Analysis of this solution by a turbidometric method indicated it contained 68 micrograms per gram potassium sulfate.

This solution (11.88 kg) was poured into two stainless steel trays and dried in the oven. After drying at 110° C. and ca. 300 mm Hg (39.99 kPa) with an air purge, the white solid was broken up. Analysis of a sample by $^1$H NMR analysis indicated the acetone content was 0.0045 weight percent (45 micrograms/g). The entire sample was dried for an additional 19 h to give 5.096 kg of TFESK.

Comparative Example A

This comparative example demonstrates the recrystallization of TFESK from aqueous potassium sulfite solutions. The solubility of TFESK in water at 0° C. is 25% by weight, but in 2M $K_2SO_3$ solution it is only 1-2% by weight, whereas the solubility of $K_2SO_3$ is relatively temperature independent. Therefore, TFESK was selectively crystallized from sulfite solutions.

Saturated solutions of TFESK in 1.5M or 3.0M $K_2SO_3$ were made and used to model the direct isolation of TFESK from reaction solutions by recrystallization. The solutions were cooled, filtered, and the filter cake washed as indicated in Table I.

TABLE I

| Test No. | Molar Conc. $K_2SO_3$ | % TFESK Yield | % TFESK Purity | % Inorganic salt | Comments |
|---|---|---|---|---|---|
| 1 | 3.0 | 72 | 92 | 8 | No water wash |
| 2 | 3.0 | — | 96 | 4 | Second crop from Test 1 |
| 3 | 3.0 | 50 | 98.5 | 1.5 | Solution cooled, diluted with water. Filter cake water-washed. |
| 4 | 1.5 | 36 | 96 | 4 | Washed with water |
| 5 | 1.5 | — | 96 | — | Filter cake from Test 4 washed with water |
| 6 | 1.5 | — | 96 | — | Filter cake from Test 5 washed with water |

In Test No. 1 a 3.0M potassium sulfite solution was cooled and filtered. The precipitated TFESK was collected and analyzed and found to contain 8% inorganic salt. The aqueous filtrate was cooled to grow a second crop of crystals; this product contained 4% inorganic salt. Test No. 3 showed that diluting the cooled solution gave a purer product, but the inorganic salt content was still 1.5° A). In Test 4 a lower concentration of potassium sulfite was used which resulted in lower recovery of TFESK, but with purity of only 96%. Successive washing of the collected TFESK with water did not give a purer product. Thus, isolation of TFESK by recrystallization gave products containing high levels of inorganic contaminants.

Comparative Example B

This comparative example demonstrates the recovery of TFESK from acetone. A 5 liter three-neck round bottom flask was equipped with a mechanical stirrer, a TC well, and a condenser connected to a nitrogen bubbler. The flask was charged with crude TFESK (482.2 g, containing about 10 weight percent potassium sulfate) and acetone (2,180 g). The flask was sealed, stirred at 300 rpm, and heated to 40-43° C. for 3.5 hours.

The mixture was then filtered to give a cloudy filtrate. The solid retained on the frit was washed with 200 g of acetone. The solid was collected in a beaker, allowed to dry in the hood, and then dried in the oven to give 57.0 g of acetone-insoluble solid. The combined filtrates were re-filtered through Celite™ filter aid. The resulting clear filtrate was then rotary-evaporated to give a white, finely crystalline solid (450 g) which was dried over night in an nitrogen-purged oven at 102° C. to give 416.3 g of TFESK acetone solvate. $^1$H NMR analysis indicated that the product contained 2.79 wt % acetone. Ion chromatography analysis indicated that concentrations of sulfate, sulfite, and chloride were below the detection level of 10 micrograms per gram. A sample of this product was re-dried in an air-purged oven for 22 h at 106-112° C. $^1$H NMR analysis indicated that the product contained 1.59 wt % acetone.

In Example 1, wherein acetone was used as the solvent, but water was then used as a diluent after extraction prior to the isolation step, only a trace of acetone was present in the sample. In Example 2, wherein acetone was used as the solvent, but water was then used as a diluent after extraction prior to the isolation step, the product was found to contain 0.021 wt % acetone. Thus the use of water is needed when acetone is used as the solvent in order to obtain low levels of solvent contaminant.

Example 4

This example demonstrates the purification of crude HFPSK by acetone extraction in the presence of water. Pure HFPSK was obtained by extracting the crude product prepared as described above with acetone containing 1 weight % water. A 12 L three-neck flask equipped with a mechanical stirrer, Vigreux column connected to a nitrogen bubbler, and a glass T/S stopper was charged with crude HFPSK (982 g), acetone (from drum, 5476 g), and water (deionized, 56.3 g). The mixture was stirred for 2 h at room temperature. The contents of the flask were twice-filtered and the final filtrate evaporated to a white solid using a rotary evaporator. The product was dried in a nitrogen-purged oven at 99-105° C. for 29 h (720 g). Analysis of the product by $^1$H NMR indicated that it contained 0.026 weight percent acetone (260 micrograms/g). Analysis of the product by ion chromatography indicated that the concentrations of sulfite and chloride were below the detection limit of 10 ppm. The concentration of sulfate was determined to be 349 ppm.

Example 5

This example demonstrates purification of crude TFESK by acetone extraction followed by distillation in the presence of o-xylene diluent and water. A 1 L 4-neck round bottom flask equipped with mechanical stirring and a cold water condenser was charged with a mixture of crude TFESK (90 g, 0.41 mole) and reagent grade acetone (600 mL). The mixture was heated to 50° C. with stirring for 2 hours and then vacuum-filtered through a Celite™ pad to remove the insoluble $K_2SO_4$. The filtrate was then transferred to a clean flask equipped with mechanical stirring, a twelve inch jacketed Vigreux column, and a distillation head fitted with a cold water condenser and a 1 L receiving flask. o-Xylene (150 mL) was added to the solution of TFESK in acetone. The acetone was then distilled at atmospheric pressure as the pot temperature was increased to 100° C.; the recovered distillate weighed 476 g (602 mL). Water (25 mL) and o-xylene (25 mL) were then added to the distillation pot and a slight vacuum (630 mm Hg, 83.99 kPa) was applied to the system. Any remaining acetone and the o-xylene/water azeotrope were distilled. The pot was cooled to room temperature and filtered. The resulting solids were air-dried for 24 hours to give 70.2 g of TFESK. NMR analysis indicated 0.025 weight percent (250 micrograms/g) acetone; the sulfate concentration was less than 40 micrograms/g.

Example 6

This example demonstrates purification of crude TFESK by methanol extraction followed by distillation in the presence of o-xylene diluent without added water. A 1 L 4-neck round bottom flask equipped with mechanical stirring and a cold water condenser was charged with crude TFESK (90 g, 0.41 mol; containing about 10 weight percent $K_2SO_4$) and reagent grade methanol (400 mL). The mixture was stirred at 50° C. for two hours and filtered to collect the $K_2SO_4$. The filtrate was then placed back into the round bottom flask along with o-xylene (200 mL). The mixture was then distilled at atmospheric pressure to remove methanol. After removal of methanol, the pot was cooled to room temperature and pure TFESK was recovered from the o-xylene by filtration. The TFESK was air-dried for 24 hours. The final weight of TFESK was 79 g; the sulfate content was <40 micrograms/g. $^1$H NMR analysis of the isolated TFESK indicated it contained about 0.20 weight percent o-xylene; no methanol was observed. The o-xylene diluent and methanol solvent could be recycled in further extractions.

Comparative Example C

This example demonstrates recovery of TFESK from acetone/xylene mixtures. Crude TFESK (containing about 10% K₂SO₄) and reagent grade acetone (600 mL) were charged to a flask equipped with mechanical stirring. The mixture was heated at 50° C. for 2 hours, cooled to 40° C., and then vacuum-filtered through a Celite™ pad to collect the K₂SO₄. The filtrate was then combined with o-xylene (200 mL) and then distilled at atmospheric pressure using a 12-in Vigreux column. Distillation was terminated when the pot temperature reached 100° C. After cooling to room temperature, TFESK was filtered off from the o-xylene. The extraction and distillation/recovery process was repeated five times using recycled acetone solvent and o-xylene diluent. The TFESK was dried in air and then placed in a nitrogen-purged vacuum oven at about 88° C. for 10 hours. Analysis of the product by $^1$H NMR indicated the TFESK was contaminated with 4.4 weight percent acetone.

In comparison, in Example 5, wherein the solvent was acetone, and the diluent was o-xylene and water, NMR analysis indicated 0.025 weight percent acetone; and the sulfate concentration was less than 40 ppm. In Example 6, wherein the solvent was methanol, and the diluent was o-xylene, analysis of the isolated TFESK indicated it contained about 0.20 weight percent o-xylene; and no methanol was observed. Thus when acetone is used as the solvent, there is a need for water to be present to prevent the acetone from being incorporated into the TFESK crystal structure.

Examples 7-16

These examples demonstrate purification of TFESK in methanol, with recycle of the recovered solvent. A mixture was prepared by combining 650 g (3 mol) of crude TFESK, prepared as described above, and 2 L of anhydrous methanol in a 5 L 4-neck round bottom flask equipped with mechanical stirring, N₂ blanket, and a cold water condenser. While stirring, the reaction mixture was heated to 50° C. for 2 hours, then cooled to no lower than 40° C. To remove the insoluble K₂SO₄, the reaction mixture was vacuum filtered through a Celite™ pad directly into a 3 L 4-neck round bottom flask, equipped with mechanical stirring, a 5-plate Oldershaw column, and a distillation head with a 1:1 magnetic reflux splitter. To the solution of TFESK and methanol were added 1 L of o-xylene. The methanol was distilled at atmospheric pressure, at a 1:1 reflux ratio, to a pot temperature of 90° C. Upon removal of methanol and xylene, the pot was cooled to room temperature and filtered; solids were air dried for 24 h. Upon analysis by ion chromatography the residual potassium sulfate was less than 300 micrograms/g for each of Examples 7-16. The results are listed in Table 2. The recovered methanol and xylene from each example was recycled into the following example. The recovered methanol and xylene from Example 7 was used in Example 8; the methanol and xylene removed from Example 8 was used in Example 9; and likewise for each successive example up to example 16. The recovered TFESK from Examples 10, 11 and 12 were combined and analyzed for residual metals and solvents. The analysis of residual metals was by inductively coupled plasma spectroscopy, and the analysis of residual solvents was by H$^1$ and F$^{19}$ HMR. The results are listed in Tables 3 and 4.

TABLE 2

| Sulfate | |
|---|---|
| Example | Sulfate, microg/g |
| 7 | Less than 30 |
| 8 | Less than 30 |

TABLE 2-continued

| Sulfate | |
|---|---|
| Example | Sulfate, microg/g |
| 9 | Less than 30 |
| 10 | Less than 30 |
| 11 | Less than 30 |
| 12 | Less than 30 |
| 13 | Less than 30 |
| 14 | Less than 30 |
| 15 | Less than 30 |
| 16 | Less than 30 |

TABLE 3

| Residual metals | |
|---|---|
| Metal | Microgm/g |
| Ca | 7 |
| Cu | 7 |
| Fe | 3 |
| Na | 86 |
| P | 5 |
| Si | 5 |
| Zn | 8 |
| Metal | Weight % |
| K | 17.70 |
| S | 13.70 |

TABLE 4

| Residual solvents | |
|---|---|
| Methanol | none detected |
| o-Xylene* | 0.25% |

*easily removed via vacuum oven bake

Example 17

This example demonstrates the removal of acetone from TFESK after grinding of the soild TFESK. A sample of TFESK acetone solvate containing 4.36 weight percent acetone was ground in a large ceramic mortar and pestle. The sample was placed in a nitrogen-purged oven for 16.5 h at 173-175° C. The sample was removed from the oven, agitated with a spatula, and then replaced in the oven for an additional 5 h. Analysis of the dried product by $^1$H NMR indicated that TFESK contained 0.039 weight percent acetone. The result is listed in Table 5.

Example 18

This example demonstrates the removal of acetone from TFESK after grinding of the soild TFESK. A 500 gram sample of TFESK acetone solvate containing 3.5 weight percent acetone was ground in a six-hammer grinder and passed through a 0.039 inch round-hole screen. A portion of the ground material was heated to 170° C. in a nitrogen-purged oven (atmospheric pressure) for 24 hours. Re-analysis of the ground and dried product by $^1$H NMR indicated the acetone level had decreased to 0.02 weight percent. The result is listed in Table 5.

Comparative Examples D-H

Samples of TFESK containing acetone in the amounts listed in Table 5 were dried at the temperature and times listed in Table 5 with no prior grinding of the samples. The amount of residual acetone in the recovered TFESK sample for each condition is listed in Table 5.

TABLE 5

| Example No. | Initial Weight % Acetone | Oven Temp and Time | | Final Weight % Acetone |
|---|---|---|---|---|
| | | Temp, °C. | Time, h | |
| Comp. D | 4.63 | 164-173 | 4.25 | 0.64 |
| Comp. E | 1.59 | 153-172 | 4 | 1.35 |
| Comp. F | 1.59 | 186-190 | 5.6 | 0.80 |
| Comp. G | 5.24 | 153-172 | 4 | 4.95 |
| Comp. H | 5.24 | 186-190 | 5.6 | 3.88 |
| 17 | 4.36 | 173-175 | 21.5 | 0.039 |
| 18 | 3.50 | 170 | 24 | 0.020 |

The effect of heating samples of TFESK containing acetone without grinding of the samples and with grinding of the samples is shown in Table 5. Although heating the acetone solvate to temperatures above 150° C. reduced the amount of acetone in the TFESK, grinding the sample prior to heating as in examples 17 and 18 was particularly effective to reduce the acetone in the TFESK to a lower level.

What is claimed is:

1. A process for the purification of fluoroalkanesulfonate salts comprising
   (a) contacting a mixture comprising
      1) at least one fluoroalkanesulfonate salt of the formula $$[C(H)(F)(X)CF_2SO_3]_y M \quad (I)$$

wherein
      X is H, Cl, F, $CF_3$, or OR;
      R is $C_1$-$C_6$ alkyl, fluoroalkyl, or perfluoroalkyl;
      M is Li, Na, K, Cs, Rb, Ca, or Ba; and
      y is a positive integer equal to the valence of M; and
      2) at least one inorganic salt contaminant,
      with one or more solvents to selectively dissolve at least a portion of said salt in solution; and
   (b) isolating the solution from the mixture to yield a fluoroalkanesulfonate salt containing less than 500 micrograms of inorganic salt contaminant per gram of fluoroalkanesulfonate salt, or containing less than a maximum of 0.3% by weight of individual solvent.

2. The process of claim 1 further comprising drying the solution of fluoroalkanesulfonate salt.

3. The process of claim 1 wherein the solvent is methyl ethyl ketone, methanol, ethanol, isopropanol, acetonitrile, ethyl acetate, tetrahydrofuran, 1,2-dimethoxyethane, and dimethyl carbonate, or mixtures thereof.

4. The process of claim 1 wherein the contaminant is one or more M-salt contaminants selected from the group consisting of chlorides, fluorides, hydroxides, carbonates, hydrogen carbonates, sulfates, sulfites, hydrogen sulfites, borates, phosphates, monohydrogen phosphates, and dihydrogen phosphates wherein M is Li, Na, K, Cs, Rb, Ca, or Ba.

5. The process of claim 1 further comprising after the contacting of step (a) and prior to the isolating of step (b), mixing said solution of fluoroalkanesulfonate salt with a diluent.

6. The process of claim 5 wherein the fluoroalkanesulfonate salt is insoluble in the diluent, and the diluent has a boiling point greater than the solvent.

7. The process of claim 5 wherein the diluent is at least one of alkanes, arenes, halogenated hydrocarbons, halogen-substituted arenes, aliphatic ethers, aliphatic esters, aliphatic carbonate esters, and aliphatic ketones, each having a boiling point greater than about 90° C. and less than about 150° C., or mixtures thereof.

8. The process of claim 5 wherein the diluent further comprises water.

9. The process of claim 5 wherein the solvent is acetone and the diluent is water, or a mixture of water and xylene.

10. The process of claim 5 further comprising after the solvent removal, isolating the fluoroalkanesulfonate salt by filtration, evaporation, or centrifuging.

11. The process of claim 1 wherein the contaminant contains sulfite and sulfate salts.

12. The process of claim 11 wherein prior to contacting the mixture with a solvent in step (a), said mixture is contacted with water and an oxidizing agent to convert the sulfite and bisulfite salts to sulfate salts, followed by removal of the water.

13. The process of claim 12 wherein the oxidizing agent is air, oxygen, hydrogen peroxide, persulfate salt, sodium hypochlorite, chlorine, or chlorine dioxide.

14. The process of claim 12 wherein removal of water is by evaporation, freeze-drying, spray-drying, azeotropic drying, or vacuum stripping.

15. The process of claim 1 wherein steps (a) and (b) are repeated in sequence two or more times.

16. The process of claim 1 further comprising after step (b) recovery of the used solvent and recycling the solvent back into step (a) of the process.

17. The process of claim 5 further comprising after step (b) recovery of the used diluent and recycling the diluent back into the process.

18. The process of claim 2 wherein after drying, the salt is ground to a particle size having a maximum diameter of about 1 mm, and heated to a temperature of a minimum of 150° C. to further reduce the level of solvent.

* * * * *